United States Patent [19]

Gajda et al.

[11] Patent Number: 5,463,161
[45] Date of Patent: * Oct. 31, 1995

[54] OLEFIN ISOMERIZATION PROCESS

[75] Inventors: Gregory J. Gajda, Mount Prospect; Paul T. Barger, Arlington Heights, both of Ill.

[73] Assignee: UOP, Des Plaines, Ill.

[ * ] Notice: The portion of the term of this patent subsequent to Jul. 21, 2009 has been disclaimed.

[21] Appl. No.: 121,860

[22] Filed: Sep. 17, 1993

Related U.S. Application Data

[63] Continuation-in-part of Ser. No. 995,471, Dec. 22, 1992, Pat. No. 5,336,831, which is a continuation-in-part of Ser. No. 814,167, Dec. 30, 1991, Pat. No. 5,191,146, which is a continuation-in-part of Ser. No. 670,139, Mar. 15, 1991, Pat. No. 5,132,484, which is a continuation-in-part of Ser. No. 442,879, Nov. 29, 1989, abandoned.

[51] Int. Cl.[6] .............................. C07C 5/22; C07C 5/23; C07C 5/25; C07C 5/27
[52] U.S. Cl. ........................ 585/671; 585/667; 585/670
[58] Field of Search ................................ 585/667, 670, 585/671

[56] References Cited

U.S. PATENT DOCUMENTS

| | | |
|---|---|---|
| 2,537,283 | 1/1951 | Schaad . |
| 3,211,801 | 10/1965 | Holm et al. . |
| 3,270,085 | 8/1966 | Noddings et al. . |
| 3,304,343 | 2/1967 | Mitsutani . |
| 3,327,014 | 1/1964 | Noddings et al. . |
| 3,448,164 | 6/1969 | Holm et al. . |
| 3,723,564 | 3/1973 | Tidwell et al. . |
| 3,751,502 | 8/1973 | Hayes et al. . |
| 3,800,003 | 3/1974 | Sobel . |
| 3,972,832 | 8/1976 | Butler et al. . |
| 4,440,871 | 4/1984 | Lok et al. ............................ 502/214 |
| 4,503,282 | 3/1985 | Sikkenga ............................ 585/671 |
| 4,554,143 | 11/1985 | Messina et al. ..................... 423/306 |
| 4,567,029 | 1/1986 | Wilson et al. ....................... 423/306 |
| 4,593,146 | 6/1986 | Johnson et al. .................... 585/667 |
| 4,689,138 | 8/1987 | Miller ................................. 208/111 |
| 4,740,650 | 4/1988 | Pellet et al. ........................ 585/480 |
| 4,882,038 | 11/1989 | Lok et al. ........................... 208/111 |
| 5,107,050 | 4/1992 | Gaffney et al. .................... 585/671 |
| 5,132,467 | 7/1992 | Haag et al. ......................... 568/697 |
| 5,132,484 | 7/1992 | Gajda .................................. 585/667 |
| 5,136,108 | 8/1992 | Gaffney et al. .................... 568/697 |
| 5,191,146 | 3/1993 | Gajda et al. ........................ 585/667 |

*Primary Examiner*—Anthony McFarlane
*Assistant Examiner*—E. D. Irzinski
*Attorney, Agent, or Firm*—Thomas K. McBride; John F. Spears, Jr.; Richard E. Conser

[57] ABSTRACT

An improved process is disclosed for the isomerization of hindered olefins using a catalyst comprising a non-zeolitic molecular sieve. It is of particular interest to reduce alkyl substituents in the olefins with low formation of undesirable by-products.

20 Claims, No Drawings

OLEFIN ISOMERIZATION PROCESS

CROSS REFERENCE TO RELATED APPLICATION

This application is a continuation-in-part of application Ser. No. 995,471, filed Dec. 22, 1992 and now U.S. Pat. No. 5,336,831, which is a continuation-in-part of application Ser. No. 814,167, filed Dec. 30, 1991, now U.S. Pat. No. 5,191,146, which is a continuation-in-part of application Ser. No. 670,139, filed Mar. 15, 1991, now U.S. Pat. No. 5,132,484, which is a continuation-in-part of application Ser. No. 442,879, filed Nov. 29, 1989 and now abandoned, the contents of all of which are incorporated herein by reference thereto.

BACKGROUND OF THE INVENTION

1. Field of the Invention

This invention relates to an improved process for the conversion of hydrocarbons, and, more specifically for the catalytic isomerization of olefinic hydrocarbons.

2. General Background

Olefinic hydrocarbons are feedstocks for a variety of commercially important addition reactions to yield fuels, polymers, oxygenates and other chemical products. The specific olefin isomer, considering the degree of branching or position of the double bond, may be important to the efficiency of the chemical reaction or to the properties of the product. In plasticizer applications, for example, the more-linear (less-branched) isomers are more efficient in that a lower concentration is required to impart a specified softness to polyvinyl chloride.

Olefin isomers rarely are obtained in a refinery or petrochemical product in a ratio matching product demand. For example, there is a widespread need to increase the proportion of isobutene, isopentene and other tertiary-carbon olefins for production of MTBE, TAME and other ethers. In contrast, oligomerization of lower olefins produces an olefinic product which has an excessive proportion of alkyl substituents for high-quality plasticizer production. Catalytic isomerization to alter the ratio of isomers is one solution to these needs. Since isomerization competes with alternative feedstock sources as a source of desired isomers, an isomerization process must be efficient and relatively inexpensive. The principal problem facing workers in the art therefore is to isomerize olefins to increase the concentration of the desired isomer while minimizing product losses to heavier or lighter products.

3. Related Art

Processes for the isomerization of olefinic hydrocarbons are widely known in the art. Many of these use catalysts comprising phosphate. U.S. Pat. No. 2,537,283 (Schaad), for example, teaches an isomerization process using an ammonium phosphate catalyst and discloses examples of butene and pentene isomerization. U.S. Pat. No. 3,211,801 (Holm et al.) discloses a method of preparing a catalyst comprising precipitated aluminum phosphate within a silica gel network and the use of this catalyst in the isomerization of butene-1 to butene-2. U.S. Pat. Nos. 3,270,085 and 3,327,014 (Noddings et al.) teach an olefin isomerization process using a chromium-nickel phosphate catalyst, effective for isomerizing 1-butene and higher alpha-olefins. U.S. Pat. No. 3,304,343 (Mitsutani) reveals a process for double-bond transfer based on a catalyst of solid phosphoric acid on silica, and demonstrates effective results in isomerizing 1-butene to 2-butenes. U.S. Pat. No. 3,448,164 (Holm et al.) teaches skeletal isomerization of olefins to yield branched isomers using a catalyst containing aluminum phosphate and titanium compounds. U.S. Pat. No. 4,593,146 teaches isomerization of an aliphatic olefin, preferably 1-butene, with a catalyst consisting essentially of chromium and amorphous aluminum phosphate. None of the above references disclose the olefin-isomerization process using the non-zeolitic molecular sieve (NZMS) of the present invention.

The art also contains references to the related use of zeolitic molecular sieves. U.S. Pat. No. 3,723,564 (Tidwell et al.) teaches the isomerization of 1-butene to 2-butene using a zeolitic molecular sieve. U.S. Pat. No. 3,751,502 (Hayes et al.) discloses the isomerization of mono-olefins based on a catalyst comprising crystalline aluminosilicate in an alumina carrier with platinum-group and Group IV-A metallic components. U.S. Pat. No. 3,800,003 (Sobel) discloses the employment of a zeolite catalyst for butene isomerization. U.S. Pat. No. 3,972,832 (Butler et al.) teaches the use of a phosphorus-containing zeolite, in which the phosphorus has not been substituted for silicon or aluminum in the framework, for butene conversion. None of the above teach the use of NZMS for the present isomerization process, and Butler et al. discloses high yields of heavier olefins from butenes at a range of temperatures with a phosphorus-containing zeolite.

U.S. Pat. No. 4,503,282 (Sikkenga) reveals a process for converting linear alkenes to isomerized alkenes using a crystalline borosilicate molecular sieve, with examples demonstrating the conversion of linear butenes to isobutene. U.S. Pat. No. 5,132,467 (Haag et al.), filed Mar. 6, 1991, teaches a combination of two-stage etherification followed by common fractionation and olefin isomerization; the isomerization is carried out over a medium-pore metallosilicate catalyst with a range of ZSMs and MCM-22 being disclosed. The isomerization of olefins using NZMS, containing tetrahedral aluminum, phosphorus and at least one other element, has not been disclosed in the above references.

U.S. Pat. No. 5,107,050 (Gaffney et al.), filed Dec. 28, 1990, discloses butene isomerization using a MgAPSO or SAPO molecular sieve at a temperature above 900° F. U.S. Pat. No. 5,136,108 (Gaffney et al.), filed Mar. 6, 1991, teaches a combination process for producing TAME and/or TAA by reacting tertiary pentenes with methanol and/or water, distillation to separate reactants, and isomerization of $C_5$ hydrocarbons with return of branched hydrocarbons to TAME/TAA production; preferred isomerization catalysts are SAPOs and MgAPSOs.

"Non-zeolitic molecular sieves" or "NZMSs" as referenced herein include the "SAPO" silicoaluminophosphates of U.S. Pat. No. 4,440,871 (Lok et al.), the "FAPO" ferroaluminophosphates of U.S. Pat. No. 4,554,143 (Messina et al.), and the metal aluminophosphates of U.S. Pat. No. 4,567,029 (Wilson et al.) wherein the metal is at least one of Mn, Co, Zn and Mg. The application of NZMS-containing catalyst to the isomerization of a $C_8$ aromatics stream is revealed in U.S. Pat. No. 4,740,650 (Pellet et al.). U.S. Pat. No. 4,689,138 teaches a process for isomerizing normal and slightly branched paraffins using a catalyst comprising SAPO molecular sieves. The use of MgAPSO compositions for hydrocarbon conversion is taught in U.S. Pat. No. 4,882,038. However, none of these references discloses or suggests the present olefin-isomerization process.

SUMMARY OF THE INVENTION

Objects

It is an object of the present invention to provide an improved process for the isomerization of olefinic hydrocarbons. A corollary objective of the invention is to minimize product losses from an olefin isomerization process.

Summary

This invention is based on the discovery that a catalytic isomerization process using a catalyst comprising SAPO-11 demonstrates surprising efficiency in the skeletal isomerization of hexenes having two alkyl substituents to reduce the alkyl substituents in the product olefins.

Embodiments

A broad embodiment of the present invention is directed to the catalytic skeletal isomerization of olefinic hydrocarbons using a catalyst containing at least one NZMS.

In a preferred embodiment, the feedstock to catalytic isomerization comprises olefins within the range of $C_6$ to $C_{18}$. Optimally, hindered olefins are isomerized to reduce the proportion of alkyl substituents to obtain a product containing less-hindered olefins.

In another aspect, the NZMS of the catalyst comprises silicoaluminophosphates or "SAPO." In an alternative embodiment, the catalyst comprises a MgAPSO sieve.

These as well as other objects and embodiments will become apparent from the detailed description of the invention.

DESCRIPTION OF THE PREFERRED EMBODIMENTS

To reiterate, a broad embodiment of the present invention is directed to the catalytic isomerization of olefinic hydrocarbons using a catalyst containing at least one NZMS.

Process

According to the process of the present invention, an olefinic hydrocarbon feedstock is contacted with a catalyst containing at least one NZMS in a hydrocarbon isomerization zone. Contacting may be effected using the catalyst in a fixed-bed system, a moving-bed system, a fluidized-bed system, or in a batch-type operation. In view of the potential attrition loss of the valuable catalyst and of the operational advantages, a fixed-bed system is preferred. The conversion zone may be in one reactor or in separate reactors with suitable means therebetween to ensure that the desired isomerization temperature is maintained at the entrance to each reactor. Reactants may contact the catalyst in the liquid phase, a mixed vapor-liquid phase, or a vapor phase. Preferably, the reactants contact the catalyst in the vapor phase. The contact may be effected in each reactor in either an upward, downward, or radial-flow manner.

The feedstock may contact the catalyst in the absence of hydrogen or in the presence of hydrogen in a molar ratio to feedstock of from about 0.01 to about 10. "Absence of hydrogen" means that free or molecular hydrogen is substantially absent in the combined feed to the process. Hydrogen if present may be supplied totally from outside the isomerization process, or the outside hydrogen may be supplemented by hydrogen separated from reaction products and recycled to the feedstock. Inert diluents such as nitrogen, argon, methane, ethane and the like may be present either in association with hydrogen or in the absence of hydrogen. Although the principal isomerization reaction does not consume hydrogen, there may be net consumption of hydrogen in such side reactions as cracking and olefin saturation. In addition, hydrogen may suppress the formation of carbonaceous compounds on the catalyst and enhance catalyst stability.

In the group of olefinic hydrocarbons suitable as feedstock to the catalytic isomerization process of the present invention, mono-olefins having from 4 to 18 carbon atoms per molecule are suitable with mono-olefins having from 6 to 18 carbon atoms per molecule ($C_6$ to $C_{18}$) being preferred and $C_6$ to $C_{12}$ olefins being especially preferred. The mono-olefins are present in the feedstock in a concentration of from about 0.5 to 100 mass %, and preferably from about 5 to 100 mass %, with most of the balance usually comprising paraffins.

The feedstock olefins may be contained in product streams from petroleum-refining, synthetic-fuel, or petrochemical operations such as catalytic cracking, thermal cracking, steam pyrolysis, oligomerization, and Fischer-Tropsch synthesis. The olefins in the feedstock preferably are hindered olefins, or olefins with a high proportion of alkyl substituents on the carbon chain containing the double bond. Hindered olefins comprise both highly substituted olefins, having three or four alkyl substituents on the carbons comprising the double bond, and highly branched olefins, having at least the following number of alkyl substituents on the longest linear carbon chain containing the double bond of an olefin of carbon number N (even) or N* (odd):

(N/2)–1 (even number of carbon atoms)

([N*–1]/2)–1 (odd number of carbon atoms)

For example, 2,3-dimethyl-2-butene is a highly substituted olefin (four alkyl substituents on the carbon atoms comprising the double bond) and 3,3-dimethyl-1-butene is a highly branched olefin (two alkyl substituents=(6/2)–1).

The preferred process objective is debranching by skeletal isomerization of the olefins in the feedstock to reduce the proportion of hindered olefins. Skeletal isomerization reduces the proportion of either or both of highly substituted olefins and highly branched olefins, thereby increasing the proportions respectively of less-branched and less-substituted olefins.

The feedstock may require removal of polar contaminants such as sulfur, nitrogen or oxygen compounds by, e.g., extraction or adsorption to maintain isomerization-catalyst stability. Removal of dienes and acetylenes, e.g., by selective hydrogenation or polymerization, also may be desirable.

Isomerization conditions include reaction temperatures generally in the range of about 50° to 750° C., preferably from about 200° to 500° C. Reactor operating pressures usually will range from about atmospheric to 50 atmospheres. The amount of catalyst in the reactors will provide an overall weight hourly space velocity of from about 0.5 to 100 $hr^{-1}$, and preferably from about 1 to 40 $hr^{-1}$.

The particular product-recovery scheme employed is not deemed to be critical to the present invention; any recovery scheme known in the art may be used. Typically, the reactor effluent will be condensed and the hydrogen and inerts removed therefrom by flash separation. The condensed liquid product then is fractionated to remove light materials from the liquid product. The selected isomers may be separated from the liquid product by adsorption, fractionation, extraction or reaction.

Catalyst

An essential component of the catalyst of the present invention is at least one non-zeolitic molecular sieve, also characterized as "NZMS" and defined in the instant invention to include molecular sieves containing framework tetrahedral units ($TO_2$) of aluminum ($AlO_2$), phosphorus ($PO_2$) and at least one additional element (EL) as a framework tetrahedral unit ($ELO_2$). "NZMS" includes the "SAPO" molecular sieves of U.S. Pat. No. 4,440,871, "ELAPSO" molecular sieves as disclosed in U.S. Pat. No. 4,793,984 and certain "MeAPO", "FAPO", "TAPO" and "MAPO" molecular sieves, as hereinafter described. Crystalline metal aluminophosphates (MeAPOs where "Me" is at least one of Mg, Mn, Co and Zn) are disclosed in U.S. Pat. No. 4,567,029, crystalline ferroaluminophosphates (FAPOs) are disclosed in U.S. Pat. No. 4,554,143, titanium aluminophosphates (TAPOs) are disclosed in U.S. Pat. No. 4,500,651, MAPO metal aluminophosphates wherein M is As, Be, B, Cr, Ga, Ge, Li or V are disclosed in U.S. Pat. No. 4,686,093, and binary metal aluminophosphates are described in Canadian Patent 1,241,943. ELAPSO molecular sieves also are disclosed in patents drawn to species thereof, including but not limited to GaAPSO as disclosed in U.S. Pat. No. 4,735,806, BeAPSO as disclosed in U.S. Pat. No. 4,737,353, CrAPSO as disclosed in U.S. Pat. No. 4,738,837, CoAPSO as disclosed in U.S. Pat. No. 4,744,970, MgAPSO as disclosed in U.S. Pat. No. 4,758,419 and MnAPSO as disclosed in U.S. Pat. No. 4,793,833. The aforementioned patents are incorporated herein by reference thereto. The nomenclature employed herein to refer to the members of the aforementioned NZMSs is consistent with that employed in the aforementioned applications or patents. A particular member of a class is generally referred to as a "-n" species wherein "n" is an integer, e.g., SAPO-11, McAPO-11 and ELAPSO-31. In the following discussion on NZMSs set forth hereinafter the mole fraction of the NZMS are defined as compositional values which are plotted in phase diagrams in each of the identified patents, published applications or copending applications.

The preferred NZMSs are the silicoaluminophosphate molecular sieves described in U.S. Pat. No. 4,440,871. The silicoaluminophosphate molecular sieves are disclosed as microporous crystalline silicoaluminophosphates, having a three-dimensional microporous framework structure of $PO_2^+$, $AlO_2^-$ and $SiO_2$ tetrahedral units, and whose essential empirical chemical composition on an anhydrous basis is:

wherein "R" represents at least one organic templating agent present in the intracrystalline pore system; "m" represents the moles of "R" present per mole of $(Si_xAl_yP_z)O_2$ and has a value of from 0.02 to 0.3; "x", "y" and "z" represent, respectively, the mole fractions of silicon, aluminum and phosphorus present in the oxide moiety, said mole fractions being within the compositional area bounded by points A, B, C, D and E on the ternary diagram which is FIG. 1 of U.S. Pat. No. 4,440,871, and represent the following values for "x", "y" and "z":

| Point | Mole Fraction | | |
|---|---|---|---|
| | x | y | z |
| A | 0.01 | 0.47 | 0.52 |
| B | 0.94 | 0.01 | 0.05 |
| C | 0.98 | 0.01 | 0.01 |
| D | 0.39 | 0.60 | 0.01 |
| E | 0.01 | 0.60 | 0.39 |

The silicoaluminophosphates of U.S. Pat. No. 4,440,871 are generally referred to therein as "SAPO" as a class, or as "SAPO-n" wherein "n" is an integer denoting a particular SAPO such as SAPO-11, SAPO-31, SAPO-40 and SAPO-41. The especially preferred species SAPO-11 as referred to herein is a silicoaluminophosphate having a characteristic X-ray powder diffraction pattern which contains at least the d-spacings set forth below:

| SAPO-11 | | |
|---|---|---|
| 2r | d | Relative Intensity |
| 9.4–9.66 | 9.41–9.17 | m |
| 20.3–20.6 | 4.37–4.31 | m |
| 21.0–21.3 | 4.23–4.17 | vs |
| 21.1–22.35 | 4.02–3.99 | m |
| 22.5–22.9 (doublet) | 3.95–3.92 | m |
| 23.15–23.35 | 3.84–3.81 | m-s |

The MgAPSO molecular sieves of U.S. Pat. No. 4,758,419 have a framework structure of $MgO_2^{-2}$, $AlO_2^-$, $PO_2^+$, and $SiO_2$ tetrahedral units having an empirical chemical composition on an anhydrous basis expressed by the formula:

wherein "R" represents at least one organic templating agent present in the intracrystalline pore system; "m" represents the molar amount of "R" present per mole of $(Mg_wAl_xP_ySi_z)O_2$ and has a value of zero to about 0.3; and "w", "x", "y" and "z" represent the mole fractions of elemental magnesium, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.39 | 0.59 | 0.02 |
| C | 0.01 | 0.60 | 0.39 |
| D | 0.01 | 0.01 | 0.98 |
| E | 0.60 | 0.01 | 0.39 |

It is within the scope of the invention that the catalyst comprises two or more NZMSs. Preferably the NZMSs are as a multi-compositional, multi-phase composite having contiguous phases, a common crystal framework structure and exhibiting a distinct heterogeneity in composition, especially wherein one phase comprises a deposition substrate upon which another phase is deposited as an outer layer. Such composites are described in U.S. Pat. No. 4,861,739, incorporated herein by reference thereto. In a highly preferred embodiment the layered catalyst comprises a crystalline aluminophosphate of U.S. Pat. No. 4,310,440 and a SAPO, especially ALPO-11 and SAPO-11.

The NZMS preferably is combined with a binder for convenient formation of catalyst particles. The binder should be porous, adsorptive support having a surface area of about 25 to about 500 m$^2$/g, uniform in composition and relatively refractory to the conditions utilized in the hydrocarbon conversion process. By the term "uniform in composition," it is meant that the support be unlayered, have no concentration gradients of the species inherent to its composition, and be completely homogeneous in composition. Thus, if the support is a mixture of two or more refractory materials, the relative amounts of these materials will be constant and uniform throughout the entire support., It is intended to include within the scope of the present invention carrier materials which have traditionally been utilized in hydrocarbon conversion catalysts such as: (1) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, etc.; (2) ceramics, porcelain, bauxite; (3) silica or silica gel, silicon carbide, clays and silicates including those synthetically prepared and naturally occurring, which may or may not be acid treated, for example attapulgus clay, diatomaceous earth, fuller's earth, kaolin, kieselguhr, etc.; (4) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations, (5) spinels such as $MgAl_2O_4$, $FeAl_2O_4$, $ZnAl_2O_4$, $CaAl_2O_4$, and other like compounds having the formula $MO$—$Al_2O_3$ where M is a metal having a valence of 2; and (6) combinations of materials from one or more of these groups.

The preferred binder to effect a selective finished catalyst is a form of amorphous silica. The preferred amorphous silica is a synthetic, white, amorphous silica (silicon dioxide) powder which is classed as wet-process, hydrated silica. This type of silica is produced by a chemical reaction in a water solution, from which it is precipitated as ultra-fine, spherical particles. It is preferred that the BET surface area of the silica is in the range from about 120 to 160 M$^2$/g. A low content of sulfate salts is desired, preferably less than 0.3 wt. %. It is especially preferred that the amorphous silica binder be nonacidic, e.g.; that the pH of a 5% water suspension be neutral or basic (pH about 7 or above).

NZMS and binder are combined to form an extrudable dough, having the correct moisture content to allow for the formation of extrudates with acceptable integrity to withstand direct calcination. Extrudability is determined from an analysis of the moisture content of the dough, with a moisture content in the range of from 30 to 50 wt. % being preferred. Extrusion is performed in accordance with the techniques well known in the art. A multitude of different extrudate shapes are possible, including, but not limited to, cylinders, cloverleaf, dumbbell and symmetrical and asymmetrical epolylobates. It is also within the scope of this invention that the extrudates may be further shaped to any desired form, such as spheres, by any means known to the art.

An optional component of the present catalyst is a platinum-group metal including one or more of platinum, palladium, rhodium, ruthenium, osmium, and iridium. Preferably the catalyst is substantially free of a hydrogenation promoter such as a Group VIII metal which would result in economically significant losses of olefins to paraffins through hydrogenation. The preferred catalyst contains less than 100 mass parts per million (ppm) on an elemental basis of hydrogenation promoter, and optimally less than about 10 mass ppm. It is especially preferred that the catalyst be substantially free of platinum and palladium.

The catalyst of the present invention may contain a halogen component. The halogen component may be either fluorine, chlorine, bromine or iodine or mixtures thereof. Chlorine is the preferred halogen component. The halogen component is generally present in a combined state with the inorganic-oxide support. The halogen component is preferably well dispersed throughout the catalyst and may comprise from more than 0.2 to about 15 wt. %, calculated on an elemental basis, of the final catalyst.

The optional halogen component may be incorporated in the catalyst in any suitable manner, either during the preparation of the inorganic-oxide support or before, while or after other catalytic components are incorporated. For example, the carrier material may contain halogen and thus contribute at least some portion of the halogen content in the final catalyst. The halogen component or a portion thereof also may be added to the catalyst during the incorporation of other catalyst components into the support. Also, the halogen component or a portion thereof may be added to the catalyst by contacting with the halogen or a compound, solution, suspension or dispersion containing the halogen before or after other catalyst components are incorporated into the support. Suitable compounds containing the halogen include acids containing the halogen, e.g., hydrochloric acid. The halogen component or a portion thereof may be incorporated by contacting the catalyst with a compound, solution, suspension or dispersion containing the halogen in a subsequent catalyst regeneration step. The catalyst composite is dried at a temperature of from about 100° to about 320° C. for a period of from about 2 to about 24 or more hours and calcined at a temperature of from 400° to about 650° C. in an air atmosphere for a period of from about 0.1 to about 10 hours. The optional halogen component may be adjusted by including a halogen or halogen-containing compound in the air atmosphere.

EXAMPLES

The following examples are presented to demonstrate the present invention and to illustrate certain specific embodiments thereof. These examples should not be construed to limit the scope of the invention as set forth in the claims. There are many possible other variations, as those of ordinary skill in the art will recognize, which are within the spirit of the invention.

Example I

Isomerization of hindered olefins was demonstrated using a ⅞-inch stainless-steel reactor. Ten ml of catalyst as extrudate was placed in the reactor. Feedstock was charged to the reactor using a syringe pump. The reaction temperature was monitored by a thermocouple in the catalyst bed and controlled by heating the reactor in a 3-zone furnace. Furnace temperature was controlled by a thermocouple. The liquid products were analyzed by vapor-phase chromatography.

Isomerization of highly substituted and highly branched hexenes was demonstrated over SAPO-11 catalyst. SAPO-11 catalyst is characterized as described hereinabove, and the specific catalyst samples used in these tests had the following approximate properties:

| Composition, mass % | Al$_2$O$_3$ | 41.7 |
|---|---|---|
| | P$_2$O$_5$ | 50.5 |
| | SiO$_2$ | 7.8 |
| | | 100.0 |

The SAPO-11 was extruded with a silica binder to prepare a catalyst for skeletal isomerization.

Example II

The bound SAPO-11 catalyst of Example I was used to demonstrate skeletal isomerization of a highly substituted olefin. Pure 2,3-dimethyl-2-butene was isomerized at a temperature of 280° C., atmospheric pressure, a liquid hourly space velocity of 6 on olefin, and in the presence of molecular nitrogen at a gas hourly space velocity of 830. Conversion of the 2,3-dimethyl-2-butene was 43.4%. Selectivities were as follows in mass %:

| | |
|---|---|
| Dimethylbutenes | 48.2% |
| Methylpentenes | 38.2% |
| Hexenes | 6.9% |
| Paraffins | 0.3% |
| Light ends (C$_5$−) | 2.3% |
| Heavy ends (C$_7$+) | 4.1% |

Thus, conversion to C$_6$ olefins in the product was over 93% with a significant reduction in alkyl substituents.

Example III

Skeletal isomerization of a highly branched olefin was demonstrated using the SAPO-11 catalyst of Example I. Pure 3,3-dimethyl-1-butene was isomerized at a temperature of 280° C., atmospheric pressure, a liquid hourly space velocity of 6 on olefin, and in the presence of molecular nitrogen at a gas hourly space velocity of 830. Conversion of the 3,3-dimethyl-1-butene was 73.2%. Selectivities were as follows in mass %:

| | |
|---|---|
| Dimethylbutenes | 77.5% |
| Methylpentenes | 17.2% |
| Hexenes | 3.0% |
| Paraffins | 0.3% |
| Light ends (C$_5$−) | 0.7% |
| Heavy ends (C$_7$+) | 1.4% |

Thus, conversion to C$_6$ olefins in the product was over 97% with a significant reduction in alkyl substituents.

We claim:

1. A process for the skeletal isomerization of hindered olefins to reduce the proportion of alkyl substituents on the olefins which comprises contacting a feedstock containing hindered olefins at isomerization conditions with a catalyst containing at least one non-zeolitic molecular sieve to obtain a product containing a lower proportion of hindered olefins.

2. The process of claim 1 wherein the hindered olefins are selected from one or both of a highly substituted olefin and a highly branched olefin and the product olefins comprises one or both of a less-substituted olefin and a less-branched olefin.

3. The process of claim 1 wherein the hindered olefins are selected from one or more olefins within the range of C$_6$ to C$_{18}$.

4. The process of claim 1 wherein the isomerization conditions comprise a temperature of from about 200° to 500° C., a pressure of from about atmospheric to 50 atmospheres, and a weight hourly space velocity of from about 0.5 to 100 hr$^{-1}$.

5. The process of claim 4 wherein the isomerization is carried out in the presence of free hydrogen.

6. The process of claim 4 wherein the isomerization is carried out in the substantial absence of free hydrogen.

7. The process of claim 1 wherein the non-zeolitic molecular sieve is selected from the group consisting of SAPOs, FAPOs, CoAPSOs, MnAPSOs, MgAPSOs and mixtures thereof.

8. The process of claim 7 wherein the non-zeolitic molecular sieve is SAPO-11.

9. The process of claim 1 wherein the catalyst comprises an inorganic oxide matrix component.

10. The process of claim 9 wherein the inorganic oxide matrix comprises silica.

11. The process of claim 1 wherein the catalyst contains less than 100 mass ppm of a hydrogenating metal.

12. A process for the skeletal isomerization of highly substituted olefins which comprises contacting a feedstock containing the highly substituted olefins at isomerization conditions with a catalyst containing at least one non-zeolitic molecular sieve to obtain a product containing less-substituted olefins.

13. The process of claim 12 wherein the highly substituted olefins are selected from one or more olefins within the range of C$_6$ to C$_{18}$.

14. The process of claim 12 wherein the highly substituted olefins have at least three alkyl substituents on the two carbons of the double bond.

15. The process of claim 12 wherein the isomerization conditions comprise a temperature of from about 200° to 500° C., a pressure of from about atmospheric to 50 atmospheres, and a weight hourly space velocity of from about 0.5 to 100 hr$^{-1}$.

16. A process for the skeletal isomerization of highly branched olefins which comprises contacting a feedstock containing the highly branched olefins at isomerization conditions with a catalyst containing at least one non-zeolitic molecular sieve to obtain a product containing less-branched olefins.

17. The process of claim 16 wherein the highly branched olefins are selected from one or more olefins within the range of C$_6$ to C$_{18}$.

18. The process of claim 16 wherein the number of alkyl substituents on the highly branched olefins having N even carbon numbers are at least (N/2)−1 and the number of alkyl substituents on the highly branched olefins having N* odd carbon numbers are at least ([N*−1]/2)−1.

19. The process of claim 16 wherein the isomerization conditions comprise a temperature of from about 200° to 500° C., a pressure of from about atmospheric to 50 atmospheres, and a weight hourly space velocity of from about 0.5 to 100 hr$^{-1}$.

20. A process for the skeletal isomerization of highly branched and highly substituted olefins which comprises contacting a feedstock containing the highly branched and highly substituted olefins at isomerization conditions with a catalyst containing at least one non-zeolitic molecular sieve to provide a product containing less-branched and less-substituted olefins.

* * * * *